United States Patent [19]

Moshofsky

[11] 4,391,401
[45] * Jul. 5, 1983

[54] SURGICAL STAPLERS AND STAPLE

[75] Inventor: Jerome F. Moshofsky, Portland, Oreg.

[73] Assignee: Lawrence M. Smith, Lake Oswego, Oreg.

[*] Notice: The portion of the term of this patent subsequent to May 17, 1998, has been disclaimed.

[21] Appl. No.: 228,620

[22] Filed: Jan. 26, 1981

Related U.S. Application Data

[63] Continuation of Ser. No. 26,071, Apr. 3, 1979, Pat. No. 4,256,251, which is a continuation-in-part of Ser. No. 899,350, Apr. 24, 1978, abandoned.

[51] Int. Cl.$^3$ .............................................. A61B 17/04
[52] U.S. Cl. ................................ 227/19; 227/DIG. 1; 128/334 R
[58] Field of Search ............. 128/92 B, 334 R, 355.5; 72/410; 206/343, 345, 346; 227/19, 82, 83, 85, 87, 92, 120, 124, 129, 132, 140, 134, DIG. 1

[56] References Cited

U.S. PATENT DOCUMENTS

| | | | |
|---|---|---|---|
| 368,423 | 8/1887 | Remus | 227/DIG. 1 |
| 506,861 | 10/1893 | Prentice | 227/DIG. 1 |
| 1,945,377 | 1/1934 | Posnack | 227/DIG. 1 |
| 2,142,782 | 1/1939 | Gillette | 227/DIG. 1 |
| 2,744,251 | 5/1956 | Vollmer | 227/DIG. 1 |
| 3,077,812 | 2/1963 | Dietrich | 227/DIG. 1 |
| 3,307,389 | 3/1967 | Rose | 227/DIG. 1 |
| 3,604,561 | 9/1971 | Mallina | 227/120 |
| 3,643,851 | 2/1972 | Green et al. | 227/DIG. 1 |
| 3,646,801 | 5/1972 | Caroli | 227/19 X |
| 3,775,826 | 12/1973 | Reed | 227/DIG. 1 |
| 3,777,355 | 12/1973 | Cooke | 227/DIG. 1 |
| 3,827,277 | 8/1974 | Weston | 227/DIG. 1 |
| 3,837,555 | 9/1974 | Green | 227/130 |
| 3,873,016 | 3/1975 | Fishbein | 227/83 |
| 4,014,492 | 3/1977 | Rothfuss | 227/DIG. 1 |
| 4,109,844 | 8/1978 | Becht | 227/120 |
| 4,122,989 | 10/1978 | Kapitanov et al. | 227/108 |
| 4,127,227 | 11/1978 | Green | 227/83 |
| 4,166,466 | 9/1979 | Jarvik | 128/325 |
| 4,226,242 | 10/1980 | Jarvik | 227/DIG. 1 |

FOREIGN PATENT DOCUMENTS 1094230 12/1960 Fed. Rep. of Germany ... 227/DIG. 1

Primary Examiner—Paul A. Bell
Attorney, Agent, or Firm—Klarquist, Sparkman, Campbell, Leigh, Whinston & Dellett

[57] ABSTRACT

The specification discloses a forming die or ram movable along a guideway or track by a pair of toggle-joint linkages to move from a column of staples a staple having a downwardly bowed central portion into engagement with an anvil, then bend outer portions down over the anvil to drive pointed legs into the flesh and bring the legs into alignment with each other. The column of staples is pressed by a spring arm and a follower toward the track and is laterally supported in a staple magazine. Each toggle-joint linkage is a one-piece member with two rigid arms connected by an undulating spring portion. The magazine is detachably connected to the track by spring latches or clips. Another stapler has a hook-like anvil, and the bowed central portion of the staple as it is pressed against the anvil by a forming die or ram, is first straightened and then bent legs are bent from the central portion, thus giving a "soft" initial feel to the stapling.

2 Claims, 21 Drawing Figures

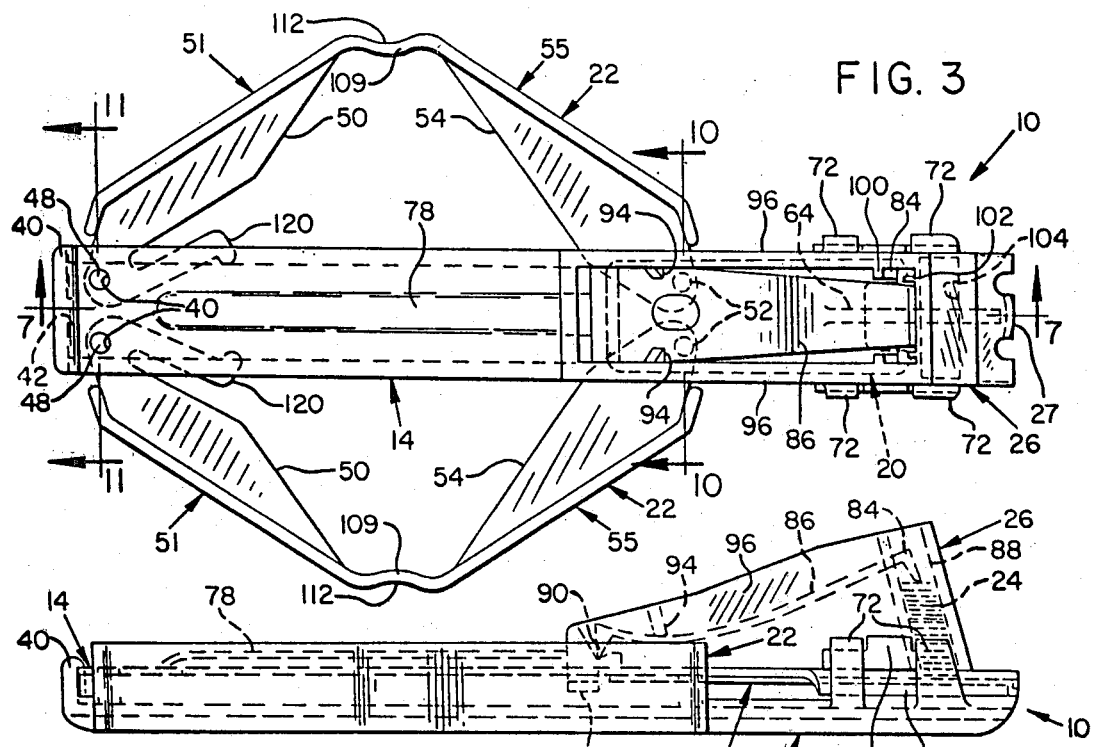
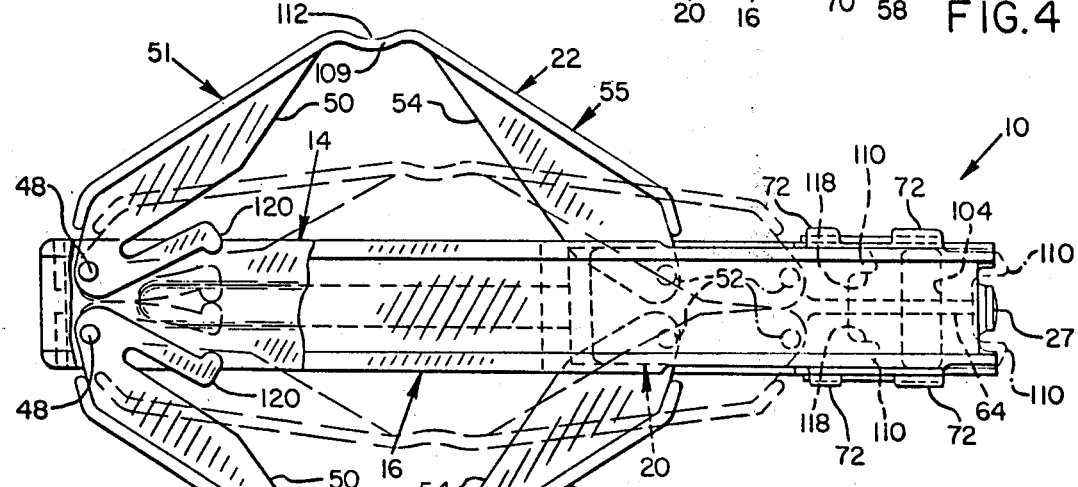
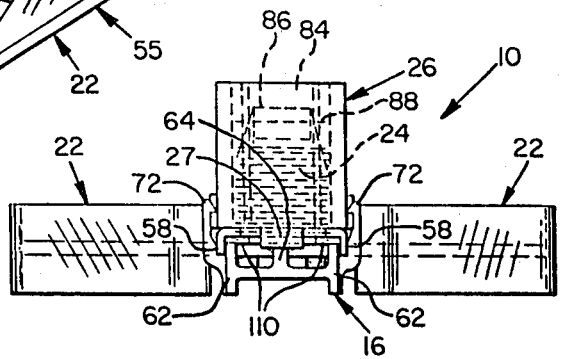

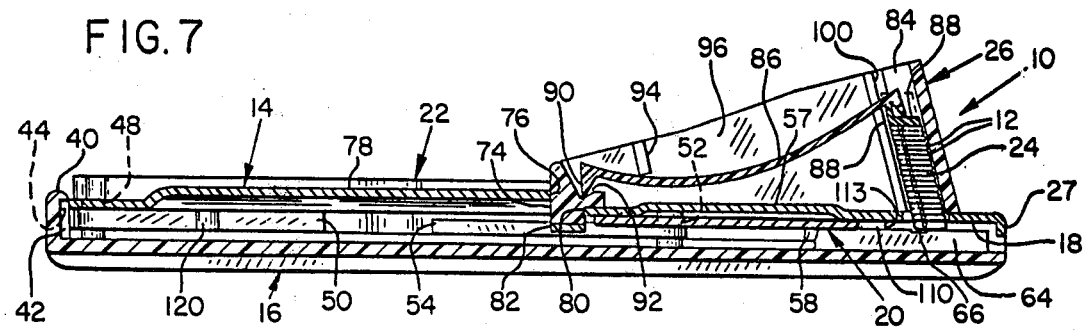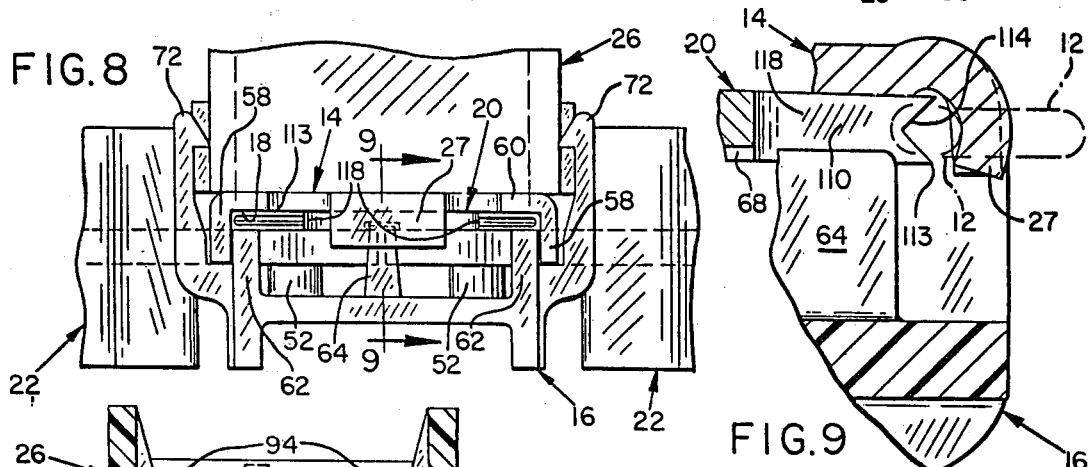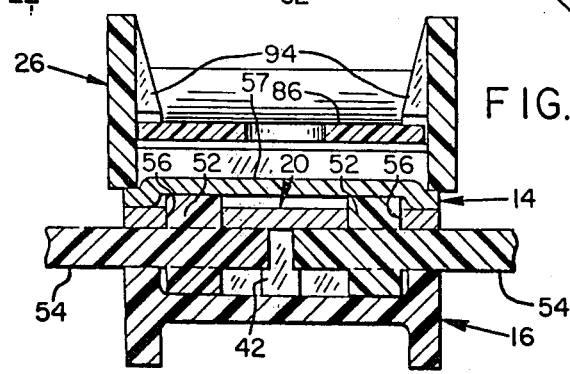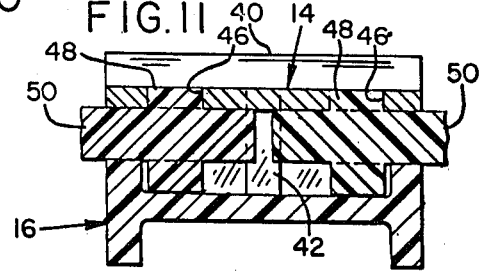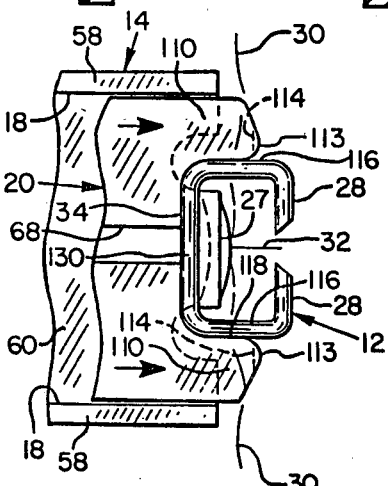

SURGICAL STAPLERS AND STAPLE

RELATED APPLICATION

This is a continuation of application Ser. No. 26,071, filed Apr. 3, 1979, now U.S. Pat. No. 4,256,251, which is a continuation-in-part of my application Ser. No. 899,350, filed Apr. 24, 1978, now abandoned.

This invention relates to improved surgical staplers and an improved surgical staple, and has for an object thereof the provision of new and improved surgical staplers and a new and improved surgical staple.

Another object of the invention is to provide surgical staplers that are very reliable yet so inexpensive that each can be discarded after one use.

Another object of the invention is to provide a surgical stapler having a magazine clipped to a cover and a base.

Another object of the invention is to provide a surgical stapler having a magazine secured to a base by spring clips which also secure a cover to the base.

A further object of the invention is to provide a surgical stapler having a pair of toggle-joint linkage handles serving to drive a staple forming ram.

Another object of the invention is to provide a surgical stapler having a magazine pressing a stack of staples toward a guideway or track having a support rib which engages the end staple of the stack to hold it from accidental movement.

Another object of the invention is to provide a surgical stapler having a sheet metal anvil cupped to strengthen it and provide a rounded contacting surface.

Another object of the invention is to provide a surgical stapler and staple in which the force of stapling is initially soft.

Another object of the invention is to provide a surgical stapler which is locked against actuation when its supply of staples has been used up.

Another object of the invention is to provide a stapler in which two arms of a ram are spaced substantially from each side of an anvil to provide good leverage in stapling.

Another object of the invention is to provide a surgical staple having a reversely bowed central portion and two legs bent from the central portion, so that by pressing the legs on opposite sides of the bowed portion, the bowed portion is first bent straight and then the legs are bent from the central portion.

In the drawings:

FIG. 3 is a top plan view of the surgical stapler of FIG. 1;

FIG. 4 is a side elevation view of the surgical stapler of FIG. 1;

FIG. 5 is a bottom plan view of the surgical stapler of FIG. 1;

FIG. 6 is a front elevation view of the surgical stapler of FIG. 1;

FIG. 7 is a sectional view taken along line 7—7 of FIG. 3;

FIG. 8 is a fragmentary, front elevation view of the stapler of FIG. 1;

FIG. 9 is an enlarged, fragmentary, vertical section taken along line 9—9 of FIG. 8;

Figures 1, 2:
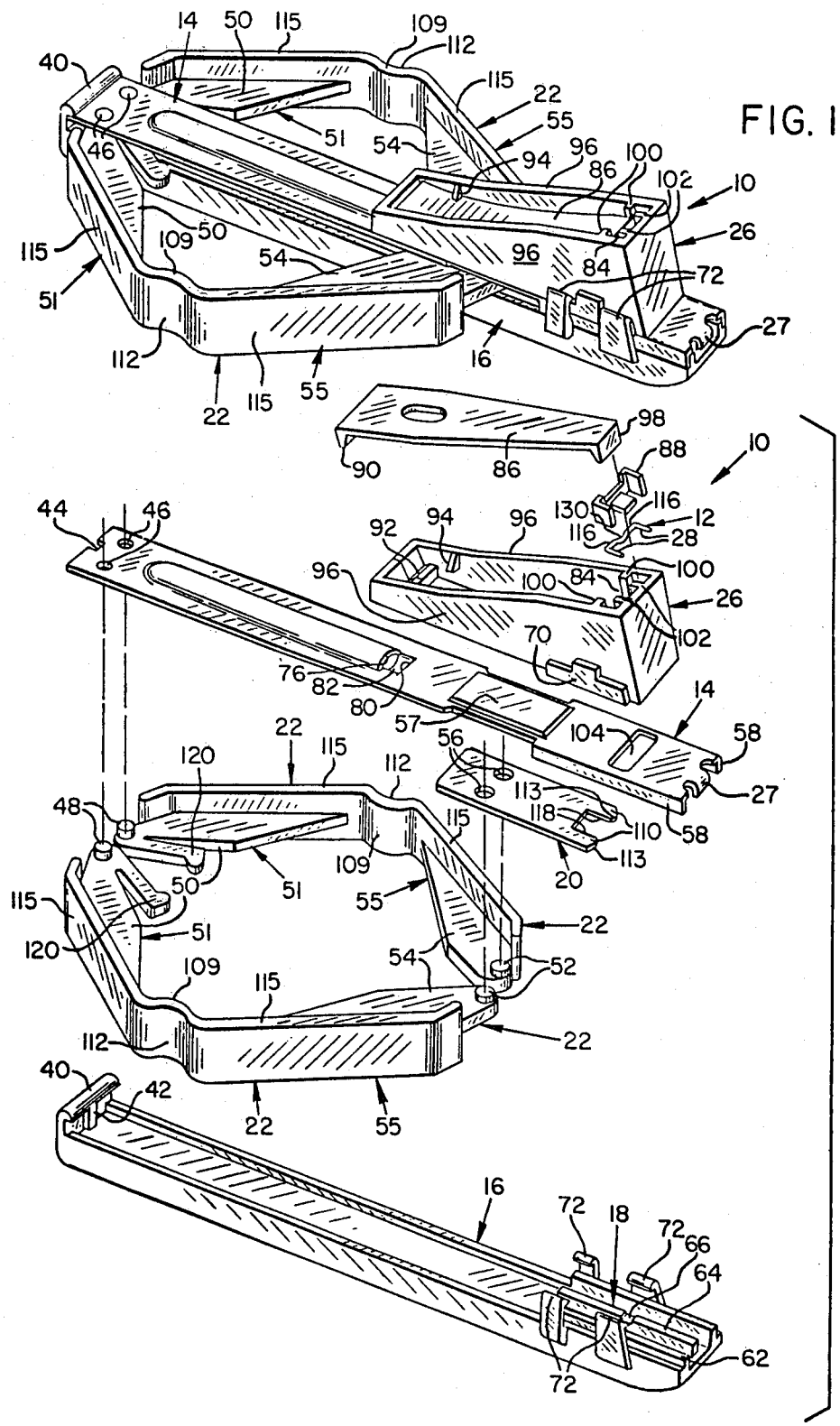
FIG. 1 is a perspective view of a surgical stapler forming one embodiment of the invention.
FIG. 2 is an exploded perspective view of the stapler of FIG. 1 and a staple forming one embodiment of the invention.
Figure 15:
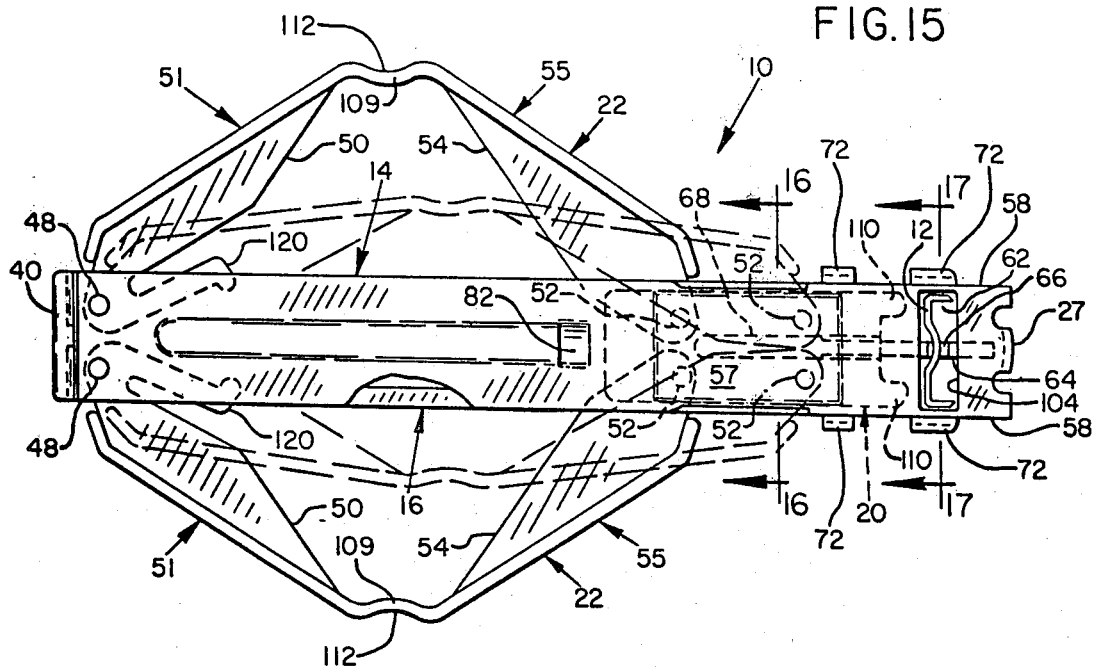
Figure 16:
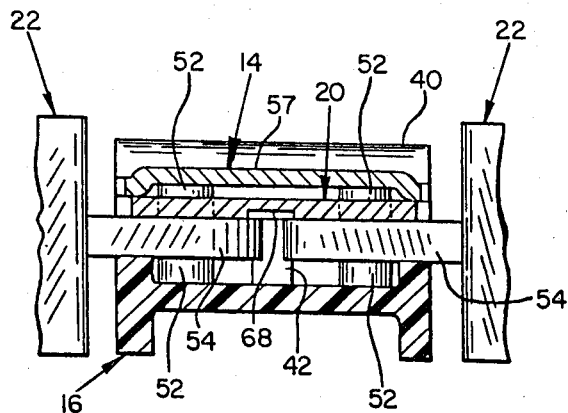
Figure 17:
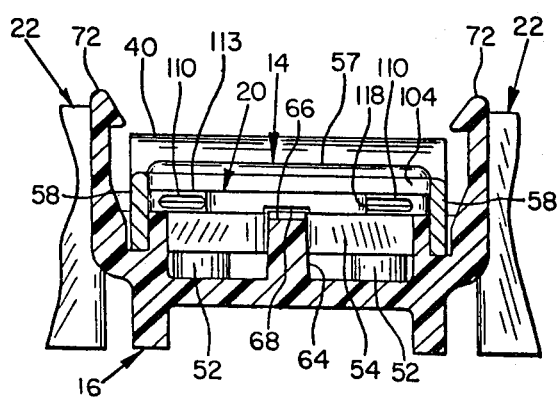
Figure 18:
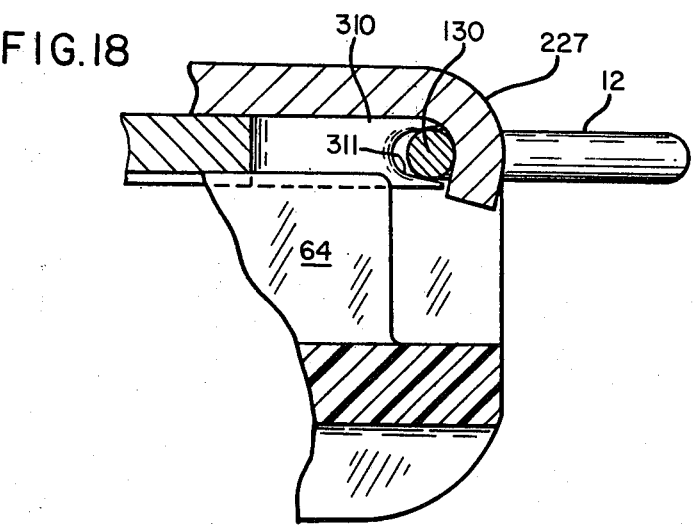
Figure 19:
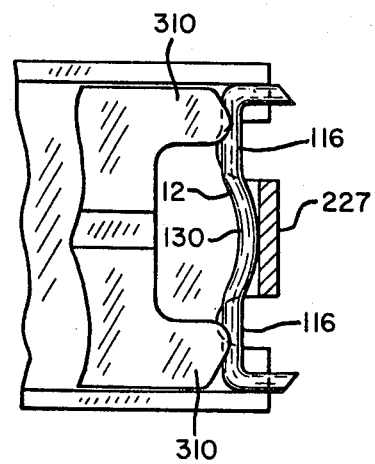
Figure 20:
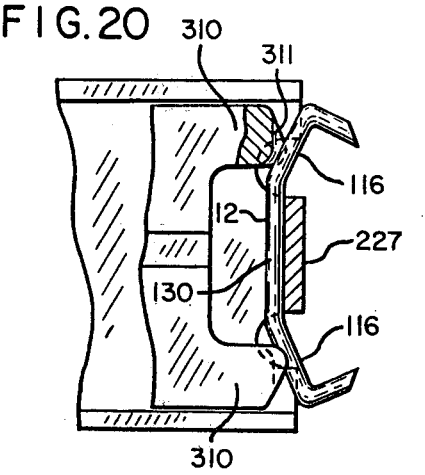
Figure 21:
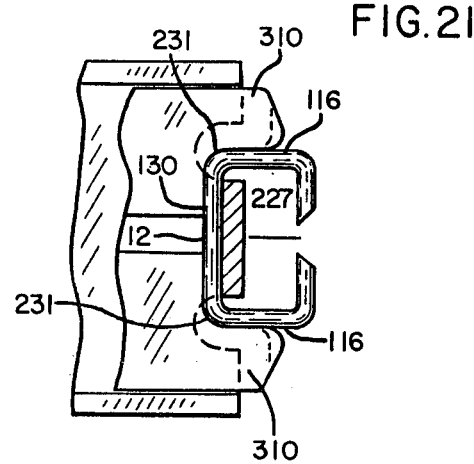

FIGS. 10 and 11 are vertical, sectional views taken along lines 10—10 and 11—11 of FIG. 1;

FIGS. 12, 13 and 14 are enlarged, fragmentary views of the stapler and staple looking upwardly during the different steps in a stapling operation;

FIG. 15 is a top plan view of the stapler with its magazine removed;

FIG. 16 is an enlarged, vertical, sectional view taken along line 16—16 of FIG. 15;

FIG. 17 is an enlarged, vertical, sectional view taken along line 17—17 of FIG. 15 but without the staple;

FIG. 18 is an enlarged, fragmentary, sectional view, like FIG. 9, but of a stapler forming an alternate embodiment of the invention; and FIGS. 19, 20 and 21 are enlarged, fragmentary views, like FIGS. 12, 13 and 14, but of the stapler of FIG. 18.

An improved surgical stapler 10 forming one specific embodiment of the invention is adapted to staple improved surgical staples 12 forming an alternate embodiment of the invention. The stapler includes a two piece body consisting of a cover 14 of stainless steel and a channel-like base 16 I-shaped in transverse cross-section and of a tough plastic material such as, for example, an acetal such as "DELRIN" or an acrylic material. The cover and the base form a guideway 18 for a plate-like die or ram 20 of stainless steel, the ram being drivable by two, identical, manually operable toggle-joint linkage handles 22 from a retracted position past a stack or column 24 of the staples in a magazine 26 to move the lowermost staple out of the stack, along the guideway and into engagement with an anvil 27 of the cover, and then form the staple around the anvil to insert pointed legs 28 of the staple into a patient 30 at opposite sides of a cut 32 to be sutured and bend top 34 of the staple to form the staple into a rectangle. Pressure on the handles is released slightly and the anvil then is slid out from under the top of the suture. Then the remaining pressure on the handles 22 is released and the handles retract the ram 20, after which another staple is moved through the magazine 26 into the guideway for another stapling operation.

The base 16 includes a hook 40 and a key 42 forming a socket-like end. The rear end portion of the cover 14 has a keying notch 44 that fits over the key permitting the rearmost portions of the cover to fit under the hook, thus interlocking the rearward ends of the cover and base. Holes 46 in the cover receive rear pins 48 on rear gussets or webs 50 of rear arms 51 of the handles 22, and front pins 52 on front gussets or webs 54 of front arms 55 of the handles fit in holes 56 in the ram 20. The cover has a raised clearance portion 57 for the pins 52. The ram is slidable between and guided by side flanges 58 of a channel-like, forwardly located guide portion 60 of the cover 14. The guideway 18 is formed by the guide portion 60 and side ribs 62 of the base 16. A staple-supporting center rib 64 is provided on the base intermediate the side ribs 62 for frictionally engaging the lowermost staple 12 to keep it from moving along the guideway except by action of the ram. The center rib has a shallow notch 66 for holding the staple against accidental movement along the guideway. The ribs 62 serve to support the legs 28 of the staple. In one constructed stapler, the height of the center rib was 0.005 inches higher than the side ribs 62. The ram 20 has a groove 68 to provide clearance for the rib 64.

The magazine 26 includes a pair of T-shaped lugs 70, which snap under hook portions of clips 72 of the base 16 to lock the cover 14 between the base and the magazine. The magazine has a tab or key 74 which extends into a hole 76 formed in the cover between a rib 78 of the cover and edge 80, a downwardly looped strap 82 being cut therefrom to form the hole 76 and also serve as a rear stop for the ram. The forward one of the clips 72 keeps the cover from moving forwardly relative to the base. The magazine 26 has a guide or chute 84 for the stack 24 of staples 12, and a leaf spring 86 of acetal or nylon presses a follower 88 against the stack to press the innermost one of the staples against the center rib 64. The leaf spring has a fulcrum tab 90 positioned in V-notch 92 and the leaf spring is trapped under lugs 94 on sidewalls 96 of the magazine. Presser tab 98 bears against the inside end of the follower, which is complimentary in shape to the chute 84. The chute 84 includes outer, angular guide members 100 guiding outer corner portions of the staple and inner ribs 102 guiding inner corner portions of the staples. The cover 14 has an opening 104 through which the stack extends. The follower 88 extends through the opening into the path of the ram 20 when the ram has been retracted after the last staple has been stapled, the follower then blocking movement of the ram, which indicates to the user that the staples have all been used.

Each linkage handle 22 includes an undulating, flexible leaf-spring portion 109 having finger or thumb recesses 112. The leaf-spring portions hingedly connected the corresponding arms 51 and 55 and form continuations of wide, strip-like portions 115 of the arms, which are rigidified by the gussets 50 and 54. The ram 20 includes a pair of forming tines 110 having rounded noses 113 and aligned, shallow grooves 114 for receiving and centering portions 116 of the staple. Edges 118 converge slightly, about 4°, toward each other proceeding rearwardly. The rear end of the notch formed by the tines acts as a stop when it presses the central portion 130 of the staple against the anvil to limit forward movement of the ram. The webs 50 preferably have spring finger portions 120 acting as cushions or shock absorbers at the end of each stapling operation so that cushioning is provided.

The portions 116 of the staple 12 that are aligned with each other and are connected to a downwardly bowed central portion 130 so that they are somewhat prebent toward each other as the central, bowed portion is bent straight during the initial forming of a stapling operation, as shown in FIG. 13. Then the portions 116 are bent to right-angles with the central portion 130.

As best shown in FIG. 9, the anvil is somewhat belled or cupped to conform to the bowed, central portion 13 of the staple, and is easily slid out from under the portion 130 after a stapling operation.

EMBODIMENT OF FIGS. 18-21

A surgical stapler 210 forming an alternate embodiment of the invention is identical to the stapler 10 except that an anvil 227 is straight, when viewed from one edge, rather than cupped and is somewhat hook-like. In the stapling operation, only the bowed central portion 130 of the staple 12 first engages the anvil and is straightened. Then the portions 116 are bent at right angles to the straightened central portion to complete the stapling. The force required to straighten the central portion is low compared to that required to make right angle bends or corners 231 so that only a "soft" initial feel or force is used to make the required actuating force gradual rather than an abrupt, high force. It should be noted that tines 310, like the tines 110, are spaced substantially from the edges of the anvil to give high leverage in forming the corners 231. Also, by having the bow and the portions 116 aligned at the start the corners 231 are already started or prebent before any stapling occurs. This causes the tines to press on sloping portions 116 after the bowed portion is straightened. The ram has rounded staple engaging portions 311 engaging the portions 116 during the formation of the corners 231. The portions 311 increase the wedging effect to keep the force low.

What is claimed is:

1. A surgical stapler comprising:
    an elongate body having forward and rearward ends, and having a longitudinally extending guideway opening through its forward end;
    a ram having a forming end portion and being mounted in said guideway with said forming end portion adjacent the forward end of the body for sliding movement along the guideway between a forward position with its forming end portion at said forward end and a retracted position with its forming end portion spaced from said forward end;
    staple-holding means attached to said body for feeding a staple into said guideway when said ram is in its retracted position;
    at least one toggle-joint linkage, said toggle-joint linkage comprising first and second arms of generally equal length, said arms having adjacent ends pivotally attached together with the end of said first arm opposite said adjacent ends being pivotally attached to said body adjacent its rearward end and the end of said second arm opposite said adjacent ends projecting toward the forward end of said body and being pivotally attached to said ram, the adjacent ends of the arms of said toggle-joint linkage being opposed and projecting away from said body when said ram is in its retracted position so that pressing the adjacent ends of the arms of said toggle-joint linkage in a direction transverse of said guideway will move said ram from its retracted to its forward position; and
    an anvil fixed to the forward end of said body and projecting across said guideway, said anvil and the forming end portion of said ram being shaped to close a staple therebetween upon movement of said ram to its forward position.

2. A surgical stapler according to claim 1 wherein said ram has a substantially greater width than thickness in directions normal to said longitudinally extending guideway, and said toggle-joint linkage is attached to said body and said ram so that the adjacent ends of said arms move in a direction gradually parallel to the width of said ram upon pressing of said adjacent ends toward each other.

* * * * *